United States Patent [19]

Cervelle et al.

[11] Patent Number: 4,460,578

[45] Date of Patent: Jul. 17, 1984

[54] **PHARMACEUTICAL COMPOSITION FOR TOPICAL USE BASED ON A TOTAL EXTRACT OF *HEDYSARUM FRUCTESCENS WILLD***

[75] Inventors: Claude M. H. Cervelle, 165, boulevard Haussmann, 75008 Paris, France; Madeleine Cervelle, Paris, France

[73] Assignee: Claude Marie Henri Cervelle, Paris, France

[21] Appl. No.: 329,863

[22] Filed: Dec. 11, 1981

[30] Foreign Application Priority Data

Dec. 11, 1980 [FR] France .................. 80 26342

[51] Int. Cl.³ .......................... A61K 35/78
[52] U.S. Cl. ................................ 424/195
[58] Field of Search ....................... 424/195

[56] References Cited

U.S. PATENT DOCUMENTS 3,928,585 12/1975 Cervelle ................... 424/195

FOREIGN PATENT DOCUMENTS

| 1201726 | 1/1960 | France | 424/195 |
| 75930 | 7/1961 | France | 424/195 |
| 1478571 | 4/1967 | France | 424/195 |

OTHER PUBLICATIONS

Chemical Abstracts, vol. 90, No. 19; May 7, 1979, pp. 300-301, Ref. 148438c; Columbus, Ohio (US) & Plant. Med. Phytother 1978, 12(2), 144-147 Linard A. et al: "Flavanoids from *Lespedeza capitata* Michaux".

Chemical Abstracts, vol. 72, No. 26, Jun. 29, 1970, p. 271, Ref. 136325d; Columbus, Ohio (US) & Boll. Chim. Farm. 1969, 108(10), 587-593 Calo, Aldo: "Separation, Determination and Evaluation of *Lespedeza capitata* Flavones".

"Topical Treatment of Virus Disorders of the Mucous Membrane of the Mouth with Chelepine", (Russian Review Stomatologija-S.S.S.R. 1976-55-No. 1-pp. 100-101) plus English translation.

Treatment with Chelepine of Certain Skin Disorders of Virus Origin" E. V. Verbenko, I. L. Petrova, L. I. Goncharova, A. V. Dubarev, English translation, Vestnik Dermatol; i Venerol., (1979), No. 6, pp. 51-53.

*Primary Examiner*—Jerome D. Goldberg
*Assistant Examiner*—John W. Rollins
*Attorney, Agent, or Firm*—Oblon, Fisher, Spivak, McClelland & Maier

[57] ABSTRACT

The present invention relates to a pharmaceutical composition for topical use based on a total extract of *Hedysarum Fructescenes Willd*. This composition consists essentially of a combination of flavonoids, catechic tannins, and phenols-acids, devoid of alkaloids, in association with a pharmaceutically acceptable vehicle suitable for topical administration.

Application: treatment of tegumentary virus disorders such as herpes zona and varicella.

19 Claims, No Drawings

PHARMACEUTICAL COMPOSITION FOR TOPICAL USE BASED ON A TOTAL EXTRACT OF *HEDYSARUM FRUCTESCENS WILLD*

The present invention relates to a pharmaceutical composition for topical use based on a total extract of *Hedysarum Fructescens Willd* (papilionaceous plants), said composition being useful in particular for the treatment of tegumentary virus disorders, and in particular for the treatment of herpes, zona and varicella.

*Hedysarum Fructescens Willd* (papilionaceous plants), also termed *Lespedeza capitata* Michaux, is a leguminous flavonoid plant. It comes from North America. Its culture started in France in 1950 in the "Val de Loire" from seeds coming from North America. This plant contains as essential constituents: flavonoids, tannins, and acid-phenols. For more details concerning this plant and its constituents, reference may be made to the work of Alain G. CHARLES entitled "Contribution to the study of leguminous flavonoid *Lespedeza capitata* Michaux," Edition André Lesot (1962) Paris. The chemical study of the flavonoids of this plant was the subject of the thesis presented on Oct. 27, 1978 by Alain LINARD for the obtainment of the third cycle Doctor's degree in the pharmaceutical disciplines (René Descartes University of Paris). On this subject, there may also be cited the article of Mr. TIN WA in LLOYDIA, 32 (4), p.509-11 (1969) which concerns the isolation and the identification of Kampferitrin from *Lespedeza capitata*; this substance is one of the flavonoids contained in *Lespedeza capitata*.

As references illustrating the state of the art, it may be also cited FR Pat. Nos. 1,478,571 and 1,201,726 (with its patent for addition 75 930). FR Pat. No. 1,478,571 relates to a process for obtention in dry state or in aqueous solution of watersoluble active principles of plants of certain classes. It is mentioned in the specification of this patent that the principle of the process consists in removing, by physical means, the indesirable substances, such as tannins, fatty acids, pigments, in order to preserve only the pharmaceutically active substances, such as alkaloids in the state of flavonoid salts. *Lespedeza capitata* Michaux is cited as exemple of plants. Thus, FR Pat. No. 1,478,571 concerns the obtention of an extract from which a certain number of substances is removed. It does not disclose a process for the obtention of a total extract. Furthermore, the products, object of FR Pat. No. 1,478,571 are substances, such as alkaloids and flavonoids, free from tannins, fatty acids and pigments. It is not question of a product constituted by a combination of flavonoids, tannins and acids-phenols, free from alkaloids.

FR Pat. No. 1,201,726 (and its patent for addition 75 930) relates to the obtention of flavonic derivatives from the leaves of certain plants. They do not either concern a total extract and a product containing the combination mentioned in the preceeding paragraph.

The reference "Chemical Abstracts" Vol. 90 No. 19, May 7, 1979 p.300-301 no. 148 438 c relates to an article of LINARD et al. which concerns the composition of *Lespedeza capitata*. It particularly relates to certain flavonoids of this plant, which are the object of a particular reference.

The reference "Chemical Abstracts" vol. 72 no. 26 June 29, 1970, p.271 no. 136325d relates to an article also contributing to the chemical knowledge of plant *Lespedeza capitata* and of its flavones in particular.

These both later references are limited to indications about the chemical characteristics of a plant, *Lespedeza capitata*.

It is known that certain extracts of *Lespedeza capitata* Michaux, namely the flavonoid extracts, have pharmaceutical properties and more particularly hypoazotemic and hypocholoesteremic properties. For this purpose, reference may be made in particular to the French special medecine patents (BSM)296M and 6058M and to the BE Pat. No. 670,550.

The BSM Pat. No. 296M relates to a lespedoside extracted from leaves of *Lespedeza capitata* having hypoazotemic and hypocholesteremic properties. This lespedoside contains flavonic derivatives of the plant and is devoid of tannins. It is administered by the oral or injectable, route.

The BSM Pat. No. 6058M relates to a new medecine whose active principle, termed Lespecapitoside, is a flavonoid extracted from the leaves of *Lespedeza capitata*. This Lespecapitoside is obtained by the process disclosed in French Pat. No. 1 500 157. This medecine possesses hypoazotemic and hypocholesteremic properties and protects the artery walls against lipid infiltrations. It may be administered by the oral, intraperitoneal or intravenous route.

The BE Pat. No. 670,550 relates to an injectable medecine which is obtained from *Lespedeza capitata* and is useful in particular for the treatment of hyperazotemia. This medicine is an injectable aqueous solution of a freeze-dried extract of *Lespedeza capitata* Michaux obtained by a process which yields, from certain plants, a watersoluble extract free from tannins, fatty acids and pigments but containing unaltered, pharmacologically active substances of the plant, in particular the flavonoids and the alkaloids. Thus, the extract of *Lespedeza capitata* employed in this medicine is devoid of the tannins. Moreover, the medecine is neither presented nor proposed for the purpose of topical administration.

Furthermore, HARRY H. S. FONG et a. [J. Pharm, Sci.61 (11) p.1818 (1972)] have shown that certain plants had an antitumoural activity due to the tannins. Among these plants is the *Lespedeza capitata* var.-*velutina*. The extracts of plants employed in these tests were obtained from milled plants by percolation with a 1:1 mixture of 95% ethanol and water, and then removal of the alcohol by flash evaporation. The extracts were submitted to the "Drug Research and Development branch" of the National Cancer Institute for testing their antitumoural activity; this determination was carried out in accordance with the procedure described in the Cancer Chemotherapy Reports no. 25, December 1962. According to these procedures, the products to be tested are injected by the intraperitoneal route.

Furthermore, substances coming from plants of the Lespedeza type have already been used in the local treatment of virus disorders of the skin on the mucous membrane of the mouth. Reference may be made in this respect to the Russian review STOMATOLGIOA S.S.S.R. 1976-55 no. 1 p.100–101 and to the article of E. V. VERBENKO et al in Vestik Dermatol. i.Veneral., (1979)no. 6,p.51–53. These articles relate to the treatment with Chelepin of certain skin or mouth disorders of virus origin. From the chemical point of view, the Chelepin is all of the flavanoids (kampferol, quercetin, orientin, homoorientin, lespedin, saponaretin and vitexin) isolated from *Lespedeza hedysaroids* of the leguminous family. These articles hence concern the use, in the local treatment of certain disorders, of an exclusively flavonic extract of *Lespedeza hedysaroids* which is a different species from *Lespedeza capitata;* Chromatographic tests have moreover, shown that the flavonoids of this extract were different from those of *Lespedeza capitata.*

It has now been found that the total extract of *Lespedeza capitata* Michaux of *Hedysarum Fructescens Willd,* essentially consisting of a combination of flavonoids, catechic tannis and phenols acids, devoid of alkaloids, possess excellent pharmacological properties suitable for the treatment of tegumentary virus infections, in particular herpes, zona and varicella.

The present invention relates to a pharmaceutical composition for topical use, which is particularly useful for the treatment of tegumentary virus infections, which contains, as the active ingredient a total extract of *Hedysarum Fructescens Willd* essentially consisting of a combination of flavonoids, catechic tannis and phenols-acids, this composition being devoid of alkaloids.

The extract of *Hedysarum Fructescens Willd* used in the pharmaceutical composition according to the invention is of a yellow-brown colour; this colour varies in accordance with the procedure of extraction. It is partially soluble, in particular in water and ethanol.

The total extract of *Hedysarum Fructescens Willd* may be obtained by extraction with ethyl alcohol from the dry plant, from the fresh plant from which the fats, the waxes and the chlorophyl have been previously removed or by extraction with ethyl alcohol after maceration of the fresh plant in propylene-glycol.

There will be described hereinafter, merely by way of examples, various modes of extraction of the total extract of *Hedysarum Fructescens Willd.* These various modes of obtaining the extract give comparable results as to the qualitative composition; however, the relative richness in active principles (flavonoids, catechic tannins and phenols-acids) varies in accordance with the mode of obtaining the extract. According to one obtention mode, the dry plant (aerial parts) is extracted by alcohol lixiviation, for example with 60% (in volume) ethyl alcohol. The volume of the hydro-alcoholic extract is then reduced by concentration under vacuum. The solution is allowed to settle and then filtered. The vacuum concentration is carried out until a soft consistency of the residue is obtained. After dehydration in an oven under vacuum, the extract is ground and screened; a conventional dry extract is thus obtained.

Another mode of extract obtaining consists in extracting the fresh plant (aerial parts) by alcohol lixiviation for example with 95% (in volume)ethyl alcohol. The volume of the hydro-alcoholic extract is then reduced by concentration under vacuum. An inert powder e.g. levilite, is then added in a proportion of 25% based on the dry extract calculated in the preceding step. After homogenisation, the mixture is reduced to a powder by spray drying. In this way there is obtained a total extract in the form of a spray dried product.

According to another mode of extract obtaining, the fats, the waxes and the chlorophyll may be previously removed from the plant by a treatment with different organic solvents (acetone, petroluem ether, chloroform and like products) and then the resulting product may be extracted with ethyl alcohol according to the proceeding mode above mentioned.

According to another mode of proceeding, the fresh aerial plant is crushed and treated by maceration in propylene-glycol or another glycol for about 48 hours and is then subjected to a lixiviation with alcohol and to a filtration. A glycol-alcoholic solution is thus obtained.

The characterisation of the different active principles of the total extract of *Hedysarum Fructescens Willd* employed in the composition according to the invention, namely the flavonoids, the tannins and the phenols-acids may be effected by bi-dimensional chromatography in a thin layer of cellulose.

The characterisation of the catechic tannins is effected in accordance with the method defined by HASLAM E. [Chemistry of vegetable Tannins; Academic Press, London and New York 1966] by bi-dimensional chromatography in a thin layer of cellulose. The elution is effected with the following systems;

(1) secondary butanol/acetic acid/water in a ratio by volume of 14-1-5 and (2) 6% acetic acid in water.

The development is effected by means of 5% paratoluene-sulphonic acid in ethyl alcohol and heating up to 100° C. for 2.5 minutes. The presence of catechic tannins is characterized by a brown colour.

The characterisation of the phenols-acids is also effected by a bi-dimensional chromatography in a thin layer of cellulose in accordance with the technique defined by PARIS(R.R.) and MURGU(L) ["Concerning the polyphenolic compounds of SPIRAEA CRENATA. L. "Plantes Médicinales et Phytotherapie, 4 no. 2;p.138–149; (1970) ]. The elution systems are the following:

(1) butanol/acetic acid/water in a volume ratio of 4-1-5.

(2) aceteic acid/water(volume ratio of 15/85). The development is carried out by means of 5% ferric chloride in water or by means of an ultraviolet radiation.

The presence of phenols-acids is detected by:

a blue fluorescence (in U.V. at 350 nm) or dull brown (in U.V. at 254 nm);

a blue to blue-green colour with ferric chloride;

a development with diazoted para-nitraniline followed by a second spraying with a 2% disodium carbonate solution; the colours obtained are specific to phenols-acids and they are compared with those of reference phenols-acids.

The qualitative revealing of flavonoids is effected by bi-dimensional chromatography on a thin layer of cellulose according to the method of HARBORNE and WILLIAMS [Flavone and Flavonol glycosides in Harborne (J. B.) MABRY(T. J.) and MABRY(H.). The flavonoids Chapman and Hall London 376–441 (1975)]. The elution solvents are the following:

(1)butanol/acetic acid/water in the ratio by volume of 4-1-5

(2) acetic acid/water in a ratio by volume of 15-85.

The development is effected with a 2% aluminum trichloride in 96% alcohol or with basic lead acetate (dispensary solution). The observation is carried out in ultraviolet light before and after development of the chromatograms. When the developer is aluminum trichloride, the flavonoids have a more or less intense yellow fluorescence, while when the developer is basic lead acetate, the ortho-diphenols have an orange fluorescence in ultraviolet light, whereas in respect of the other phenols, a yellow or yellow-green fluorescence is observed. For further details concerning the characterisation of the flavonoids reference may be made to the thesis of Alain LINARD mentioned before.

The quantitative analysis of the three active principles of the total extract of *Hedysarum Fructescens Willd* is carried out in accordance with the following techniques.

(1) Titration of the flavonoids

This titration is carried out in accordance with the method disclosed by HORHAMMER L. and HANSEL R. 1951 [Nachweiss and Bestimmung von Rutin neben Quercetin Arch. Pharm 284 no.56,p.276–280]. This method will be recalled hereinafter:

(a) In the case of powdered extracts, a test solution or a solution to be titrated is prepared in the following manner:

An exactly weighed test speciment of powder in the neighbourhood of 1.50 g is placed in a 150 ml beaker. 60–70 ml of boiling 70° ethyl alcohol are added. The mixture is magnetically stirred while heating for 30 minutes. The mixture is fileterd on sintered glass and the filtrate is quantitatively collected in a calibrated 100 ml flask. The sintered glass is rinced with boiling 70° alcohol. This fraction is added to the filtrate. After cooling, a volume of 100 ml is made up with 70° ethyl alcohol. The titration is effected directly with the hydro-alcoholic extract obtained.

(b) In the case of a liquid extract, the titration is effected on the extract itself diluted to one quarter.

The reagents employed in this titration are the following:

(a) 3% zirconium oxychloride solution in water;
(b) a buffer solution obtained with the following mixture: glacial acetic acid: 24 ml
crystallized sodium acetate: 27 g
water: 200 ml
60° ethyl alcohol: 500 ml The titration of the flavonoids is effected in the following manner: 5 ml of a buffer solution and 1 ml of 3% (W/V) zirconium oxychloride aqueous solution are added to 0.1 ml of the solution to be titrated. After 5 minutes, the optical density is measured at 400 nm with respect to a reference solution in which the solution to be titrated is replaced by 60° ethyl alcohol.

The content of flavonoids is obtained by referring to a standard curve established for a rutine concentration of 0 to 200 μg (results in g per 100 g of extract or g per 100 ml in the case of a liquid extract).

Titration of the catechic tannins

The titration of the catechic tannins (including the catechines) was carried out by means of the Stiasny reagent (2 volumes of 30% formol for 1 volume of concentrated hydrochloric acid). [According to the method described by A. CHARLES in the work "Contribution to the Study of *Lespedeza capitata* Michaux" mentioned before].

According to this method, 2 g of powdered extract are left in contact with 180 ml of water at 80° C. for 2 hours. The extract is filtered on sintered glass and the residue is washed with hot water until the obtention of a final volume of 200 ml is obtained. 100 ml of Stiasny reagent are added to the filtrate. After leaving for 24 hours, the precipitate is collected on a calibrated sintered glass, washed up to neutrality and dried at 100° C. to constant weight.

In this way, the proportion of catechic tannins (and catechines) in g per 100 g of powdered extract is obtained.

In the case of a liquid extract, 50 ml of Stiasny reagent are added to 100 ml of extract. Thereafter, the procedure is identical to that of the foregoing dry extract.

3. Titration of the phenols-acids (a) Powdered Extract

A 10% (W/V) infusion extemporaneously prepared is acidified with 10% (V/V) sulphuric acid. After cooling extraction is effected with ethyl ether. The ethereal solution is extracted with a 2% sodium bicarbonate solution (ether I). After acidification of the aqueous phase with 10% sulphuric acid, it is exhausted with ethyl ether (ether II). The ethereal fractions I and II are brought together, dried on anhydrous sodium sulphate, and evaporated up to dryness under reduced pressure. They are preserved under vacuum in the presence of phosphoric anhydride and weighed to constant weight.

A result, expressed in g per 100 g of powdered extract, is obtained.

(b) Liquid Extract

If the extract contains ethyl alcohol, 100 ml of the extract are evaporated under low pressure. The volume of the extract is brought to 100 ml with water, and then acidified with 10% sulphuric acid. Thereafter the procedure is identical to that of the foregoing powdered extract. The content of phenols-acids is expressed in g per 100 ml of extract.

The remarkable therapeutic activity of the total extract of *Hedysarum Fructescens Willd* results from the synergy between the three active principles contained in this extract: the flavonoids, the catechic tannins and the phenols-acids.

The total extract of *Hedysarum Fructescens Willd* possesses very interesting curvature properties for treating herpes, zona and also other virus disorders of the skin and mucous membranes. In contrast to some commercially available products employed in this type of treatment, the total extract of *Hedysarum Fructescens Willd* has no toxicity and no contra-indication was observed.

The total extract of *Hedysarum Fructescens Willd* effectively acts, even if the treatment is carried out only when the lesion has passed the first stage of evolution.

The total extract of *Hedysarum Fructescens Willd* may be applied by the topical route in different forms, in combination with a pharmaceutically acceptable vehicle.

Thus the composition according to the invention may be in the form of solutions e.g. aqueous solutions or hydro-alcoholic solutions containing 2 to 10% by weight of the total extract.

The composition according to the invention may also be in the form of a dermic cream, the pharmaceutically acceptable vehicle than being a penetrating excipient, such as a balanced mixture of polyglycols. These creams generally contain 2 to 10% by weight of the total extract of *Hedysarum Fructescens Willd*. The composition according to the invention may also be administered in the form of a collyre for treating ocular lesions, such as cornean herpes or ophthalmic zona.

The pharmaceutically acceptable vehicle which is suitable for the purposes of the invention is therefore a vehicle which allows a topical application and may be, in particular, water, water-alcohol mixtures, saline solutions, creams, ointments, and other solid, pasty or liquid vehicles employed in a conventional manner. There is used as a cream or ointment base, any substance or combination of substances employed for this purpose, such as the polyglycols.

The invention will be now described in more detail in the following nonlimitative illustrating examples:

EXAMPLE 1

Preparation of the total extract of *Hedysarum Fructescens Willd*

A. Conventional dry extract

100 kg of dry plants coming from Beaulieu (Loiret)-France were extracted by lixiviation with 60° ethyl alcohol by using 1000 liters of ethyl alcohol. The obtained hydro-alcoholic solution was reduced by vacuum concentration. It was allowed to settle and then filtered. After vacuum dehydration in an oven, the extract was reduced to a powder and screened. About 10 kg of extract were obtained. The characterisation of the flavonoids, of the phenols-acids and the tannins, carried out in accordance with the proceeding modes defined hereinbefore, gave a positive resultion the other hand, no presence of alkaloids was revealed.

The quantitative analysis of the thus obtained extract carried out in accordance with the proceeding modes defined hereinbefore, were substantially the following (by weight per weight of extract):

Flavonoids: 9 to 12%
Tannins: 32 to 35%
Phenols-Acids: 0.4 to 0.5%

B. Spray dried product

The equivalent of 200 kg of dry plants treated with 95% ethyl alcohol yielded 1000 liters of hydro-alcoholic extract. This hydro-alcoholic extract was reduced by vacuum concentration. Thereafter, 25% of inert powder (levilite) based on the dry extract was added. After homogeneisation, the mixture was reduced to powder by spray drying 8 kg of extract having 25% of inert powder were then obtained.

The characterisation of the active principles of this extract (flavonoids, phenols-acids, tannins) carried out in accordance in the proceeding modes mentioned hereinbefore, gave a positive result. No alkaloids were detected in the extract thus obtained.

The quantitative analysis of the extract thus obtained was the following (by weight per weight of extract):

flavonoids: 9 to 12%
phenols-acids: 0.6 to 0.9%
tannins: 38 to 40%

C. Glyco-alcoholic solution

100 kg of fresh plants also coming from BEAULIEU (Loiret) France were macerated for 48 hours in 25 kg of propylene-glycol. The product was then lixiviated with 75 kg of 30% ethyl alcohol. After having allowed it to settle, it was filtered and 100 kg of extract were obtained.

The characterisation of the active principles of this extract (flavonoids, phenols-acids, tannins), carried out in accordance with the proceeding modes mentioned hereinbefore gave a positive result. No alkaloids were detected in the extract thus obtained. The quantitative analysis of the extract thus obtained was the following (by weight per volume of extract):

flavonoids: 0.3 to 0.4%
phenols-acids: 0.03 to 0.05%
tannins: 1.0 to 1.5%

EXAMPLE 2

Clinical tests

A 5% hydro-alcholic solution of total extract obtained according to example 1(A), or a dermic cream having the same dose, was employed, the vehicle being formed by a balanced mixture of polyglycols. As the cream avoids running of the liquid, it is sometimes more practical to use. The activity of either form was substantially the same.

The application was carried out either by dabbing with the aqueous solution or by slightly massaging with the dermic cream. The treatment was carried out in each case for 2 or 3 days, or more if required, 2 to 4 times a day.

1st Case: Recurring lumbar herpes

A man aged 50 years had a recurring lumbar herpes (on average every two month, above all in winter). The outbreaks of herpes appeared to be brought on by digestive phenomena or to be a consequence of a reduced immunological resistance of the subject (e.g. tiredness or worry, coryza etc. . . . ).

The outbreaks were treated with the usual medications which resulted in only a slight shortening of the evolution of the vehicles. Herpetic vaccination was without marked effect.

The lesion was dabbed 2 to 3 times per day with the hydro-alcoholic solution according to the invention. The results obtained were the following:

In September 1978

Late application of the solution according to the invention.

The vesicles dried up within 24 hours and the scab appeared and dropped off within 3 days. The burning sensation disappeared upon the first application in the morning and it reappeared in the evening and disappeared again upon the second application and no longer returned.

The ganglionic reaction and heaviness of the leg were attenuated within 24 hours.

November 1978

Applications of the composition according to the invention at the pre-vesicle stage. There was noted a complete disappearance of the burning sensation upon the first application and the final disappearance oedematic of the oedematic tension of the skin upon the 3rd application.

February 1979

The same early treatment and the same result.

In May and October 1979 as well as in March 1980, the same early treatment was carried out and the same result was obtained.

No herpetic outbreak has been noted since March 1980.

2nd Case: Recurring herpes of the labial corner

A woman aged 58 years who had a recurring herpes of the labial corner was treated twice (in October 1979 and in March 1980); but always at a late stage since the patient only sought treatment of her herpes after formation of the vesicles. The previous outbreaks lasted about 15 days each time.

With the composition according to the invention, the vesicles were dried within 24 hours by application 3 times a day after meals. The scab dropped off 3 days after.

The burning sensation disappeared upon the first applications.

3rd Case: Recurring catamenial herpes

A woman aged 41 years had a recurring catamenial herpes. The treatment with the composition of the invention was carried out at the start of the outbreak (October 1979 and March 1980) with the dermic cream or the 5% aqueous solution.

While in the previous outbreaks, and notwithstanding localized applications with various products, the outbreak which was more or less slightly shortened gave great discomfort to the subject, it was found when carrying out the two treatments with the composition according to the invention that the lesion aborted within 48 hours with disappearance of the localised discomfort.

An outbreak in December 1979 which was treated after formation of the vesicles with the composition according to the invention, was stopped and the lesion healed within 48 hours.

When employed at an early stage in dermic herpes or herpes of the mucous membrane, the composition according to the invention (hydro-alcoholic aqueous solution or cream) aborted the lesion with no formation of vesicles; the burning sensation or itch disappeared almost immediately. Within 24 hours, the skin or the mucous membrane returned its normal state and any possible ganglionic reaction had disappeared. However, the applications should be continued for 2 or 3 days.

If the lesion was already in the vesicle stage, the application of the composition according to the invention accelerated the evolution; the drying of the vesicles and the healing require only 2 to 3 days instead of 10 to 15 days.

The burning sensation or itch disappeared almost immediately and the ganglionic reactions rapidly disappeared.

In the treatment of recurring herpes, the cure should be repeated as soon as a new herpetic outbreak appears. After a few treatments, the herpetic attacks were found to be less frequent and then disappeared.

The composition according to the invention containing 5% of the total extract (in the form of a hydroalcohol aqueous solution or dermic cream) was also used for treating zonas. In each case, a marked improvement was observed at the end of one week's treatment in the bulbous form and at the end of a longer period in the other forms. The pain was markedly alleviated.

Therefore, the invention provides a non-toxic pharmaceutical composition with no secondary effects and applicable by the topical route for the treatment of tegumentary virus disorders of the most varied types.

We claim:

1. A pharmaceutical composition comprising:
a pharmaceutically acceptable vehicle for topical administration; and
an effective amount of *Hedysarum Fructescens Willd* plant extract consisting essentially of flavonoids, catechic tannins and phenols-acids, and substantially free of alkaloids;
wherein said extract is obtained by:
extracting the dry plant with an effective amount of 30–95% alcohol to obtain a hydro-alcoholic extract;
reducing the volume of said hydro-alcoholic extract; and
drying said extract.

2. The pharmaceutical composition of claim 1 wherein the vehicle is water, a water-alcohol mixture or a saline solution.

3. The pharmaceutical composition of claim 1 wherein said pharmaceutically acceptable vehicle is a polyglycol.

4. The pharmaceutical composition of claim 1 wherein the effective amount of said *Hedysarum Fructescens Willd* plant extract is about 2 to 10% by weight of said pharmaceutical composition.

5. The pharmaceutical composition of claim 4 wherein said plant extract is contained at about 5% by weight of said pharmaceutical composition.

6. The pharmaceutical composition of claim 1 wherein said composition is in the form of a paste, a cream, a solution, an ointment or a solid.

7. The pharmaceutical composition of claim 1 wherein the process of obtention comprises the use of ethyl alcohol in the extraction step.

8. The pharmaceutical composition of claim 1, wherein the process of obtention further comprises removing fats, waxes and chlorophyl from said plant with an organic solvent prior to said alcoholic extraction.

9. The pharmaceutical composition in claim 1 wherein said extract is obtained by:
extracting the fresh plant with an effective amount of 30–95% alcohol to obtain a hydro-alcoholic extract;
reducing the volume of said hydro-alcoholic extract;
adding an inert powder in a proportion of about 25% by weight with respect to said hydro-alcoholic extract to form a suspension;
homogenizing and drying said suspension.

10. The pharmaceutical composition of claim 9 wherein the alcohol used in said extraction step is 30–95% ethyl alcohol.

11. The pharmaceutical composition of claim 1 wherein said extract is a glyco-alcoholic solution obtained by:
macerating the fresh plant in the presence of an effective amount of a glycol;
then extracting said macerated plant with an alcohol; and
filtering out the remaining solids to obtain said glyco-alcoholic extract solution.

12. The pharmaceutical composition of claim 11 wherein said alcohol used in said extraction step is 30–95% ethyl alcohol.

13. A method of treating a herpes, zona and varicella virus infection of the skin of a patient which comprises topically applying to the skin of the diseased region the pharmaceutical composition of claim 1 in an amount sufficient to reduce said infection.

14. The method of claim 13 wherein said effective amount of said plant extract is between about 2 to 10% by weight of said pharmaceutical composition.

15. The method of claim 14 wherein said effective amount of said extract is about 5% by weight of said pharmaceutical composition.

16. The method of claim 13 wherein said pharmaceutically acceptable vehicle is water, a water-alcohol mixture or a saline solution.

17. The method of claim 13 wherein said pharmaceutically acceptable vehicle is a polyglycol.

18. A method of treating ocular lesions in a patient afflicted with a corneal herpes or opthalmic zona infection, comprising:

applying to the infected region the pharmaceutical composition of claim 1 in an amount sufficient to reduce said infection.

19. A method of treating a herpes, zona or varicella virus infection in the mucose membranes of an infected patient which comprises applying to the mucose membranes of the diseased region the pharmaceutical composition of claim 1 in an amount sufficient to reduce said infection.

* * * * *